(12) United States Patent
Govari et al.

(10) Patent No.: US 11,771,594 B2
(45) Date of Patent: Oct. 3, 2023

(54) CONTROLLING INTRAOCULAR PRESSURE DURING PHACOEMULSIFICATION PROCEDURE

(71) Applicant: JOHNSON & JOHNSON SURGICAL VISION, INC., Irvine, CA (US)

(72) Inventors: Assaf Govari, Haifa (IL); Eran Aharon, Haifa (IL); Yehuda Algawi, Binyamina (IL); Ilya Sitnitsky, Nahariya (IL); Amit Fuchs, Hogla (IL)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 182 days.

(21) Appl. No.: 17/382,014

(22) Filed: Jul. 21, 2021

(65) Prior Publication Data
US 2022/0339034 A1 Oct. 27, 2022

Related U.S. Application Data

(63) Continuation-in-part of application No. 17/240,505, filed on Apr. 26, 2021.

(51) Int. Cl.
*F16K 31/06* (2006.01)
*A61F 9/007* (2006.01)
(Continued)

(52) U.S. Cl.
CPC ........... *A61F 9/00745* (2013.01); *A61M 1/73* (2021.05); *A61M 1/742* (2021.05); *A61M 1/743* (2021.05);
(Continued)

(58) Field of Classification Search
CPC .. F16K 31/0668; F16K 3/314; F16K 31/0648; F16K 31/0658; F16K 31/0686;
(Continued)

(56) References Cited

U.S. PATENT DOCUMENTS 2,884,196 A * 4/1959 Allen ................... B60H 1/2212
126/116 A
3,023,777 A * 3/1962 Collins ............... F16K 31/0606
251/332

(Continued)

FOREIGN PATENT DOCUMENTS

DE 20318275 U1 2/2004
EP 0997363 A2 5/2000
(Continued)

OTHER PUBLICATIONS

StcValve Fittings, Solenoid and Pneumatic Valves, Air Regulators, stcvalve.com, Sizto Tech Corporation (STC).

*Primary Examiner* — Shaun L David
*Assistant Examiner* — Rachael L Geiger
(74) *Attorney, Agent, or Firm* — JOHNSON & JOHNSON SURGICAL VISION, INC.

(57) ABSTRACT

A system includes (i) a solenoid valve, positioned between a handle of a probe, and an aspiration line coupled with the handle for aspirating fluids from the probe, the solenoid valve includes at least a solenoid coil and a plunger movable by the solenoid coil, (ii) a sensor, positioned between the handle and the aspiration line and configured to produce a signal indicative of a fluid metric in the aspiration line, and (iii) a controller, configured to identify, based on the signal, a vacuum surge in the aspiration line, and, in response to identifying the vacuum surge, to apply at least one current to the solenoid coil to selectively move the plunger between a first position and a second position, and to selectively
(Continued)

maintain the plunger in the first position and the second position.

20 Claims, 10 Drawing Sheets

(51) Int. Cl.
*F16K 3/314* (2006.01)
*F16F 1/36* (2006.01)
*A61M 1/00* (2006.01)

(52) U.S. Cl.
CPC ............... *A61M 2205/0288* (2013.01); *A61M 2205/3334* (2013.01); *A61M 2205/3344* (2013.01); *A61M 2210/0612* (2013.01)

(58) Field of Classification Search
CPC .. F16K 31/082; F16K 31/084; F16K 31/0651; F16K 31/0675; A61F 9/00745; A61F 9/00736; A61F 2/14–1694; A61F 9/00–08; A61F 9/007–0136; A61B 2217/005; A61B 2217/007; F16F 1/3605; F16F 2224/025
See application file for complete search history.

(56) References Cited

U.S. PATENT DOCUMENTS

| | | | |
|---|---|---|---|
| 3,202,182 A * | 8/1965 | Haviland | F02D 13/04 251/282 |
| 3,530,943 A * | 9/1970 | Taylor | A01B 15/20 172/667 |
| 4,205,593 A * | 6/1980 | Sakakibara | F02D 31/007 335/277 |
| 4,326,438 A * | 4/1982 | Ballerstein | B23D 45/12 82/53.1 |
| 4,991,957 A * | 2/1991 | Sakamoto | A61B 1/009 356/241.4 |
| 5,011,113 A * | 4/1991 | Stobbs | F16F 9/46 251/129.21 |
| 8,454,551 B2 | 6/2013 | Allen et al. | |
| 9,839,738 B2 | 12/2017 | Beauvais et al. | |
| 10,182,940 B2 | 1/2019 | Chandrakant et al. | |
| 2004/0049217 A1 | 3/2004 | Ross et al. | |
| 2004/0113113 A1 | 6/2004 | Krimmer et al. | |
| 2007/0278155 A1 | 12/2007 | Lo et al. | |
| 2008/0021377 A1 | 1/2008 | Kienman et al. | |
| 2008/0312594 A1 | 12/2008 | Urich et al. | |
| 2008/0319374 A1 | 12/2008 | Zacharias | |
| 2009/0159823 A1 | 6/2009 | Matsunaga et al. | |
| 2010/0185150 A1 | 7/2010 | Zacharias | |
| 2010/0331764 A1 | 12/2010 | Boukhny et al. | |
| 2011/0034864 A1 | 2/2011 | Dacquay et al. | |
| 2012/0109173 A1 | 5/2012 | Todd | |
| 2012/0232466 A1 | 9/2012 | Kuebler et al. | |
| 2013/0053764 A1 | 2/2013 | Jaeger-Waldau | |
| 2013/0267919 A1 | 10/2013 | Caso et al. | |
| 2013/0267933 A1 | 10/2013 | Felber | |
| 2014/0030149 A1 | 1/2014 | Takeuchi | |
| 2014/0276498 A1 | 9/2014 | Connor et al. | |
| 2015/0100045 A1 | 4/2015 | Allen et al. | |
| 2015/0332834 A1 | 11/2015 | Schudt | |
| 2017/0000573 A1 | 1/2017 | Millman et al. | |
| 2018/0187794 A1 | 7/2018 | Davis | |
| 2019/0247050 A1 | 8/2019 | Goldsmith | |
| 2020/0107958 A1 | 4/2020 | Wong et al. | |
| 2020/0179169 A1 * | 6/2020 | Agahi | H01F 7/064 |
| 2020/0360185 A1 | 11/2020 | Carter et al. | |
| 2020/0383833 A1 | 12/2020 | Schaller | |
| 2021/0000648 A1 | 1/2021 | Nallakrishnan et al. | |
| 2021/0220164 A1 * | 7/2021 | Kim | A61F 7/00 |

FOREIGN PATENT DOCUMENTS

| | | |
|---|---|---|
| JP | 2003225247 A | 8/2003 |
| WO | 2010124755 A1 | 11/2010 |
| WO | 2014151209 A1 | 9/2014 |
| WO | WO-2019209081 A1 * 10/2019 ......... A61B 18/0218 |

\* cited by examiner

CONTROLLING INTRAOCULAR PRESSURE DURING PHACOEMULSIFICATION PROCEDURE

CROSS-REFERENCE TO RELATED APPLICATIONS

This application is a continuation-in-part (CIP) of U.S. patent application Ser. No. 17/240,505, filed Apr. 26, 2021, whose disclosure is incorporated herein by reference.

FIELD OF THE INVENTION

The present invention relates to medical systems, and in particular, but not exclusively to, fluid dynamics in medical systems.

BACKGROUND

A cataract is a clouding and hardening of the eye's natural lens, a structure which is positioned behind the cornea, iris and pupil. The lens is mostly made up of water and proteins and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution (BSS) to maintain the anterior chamber of the eye. After removing the cataract with phacoemulsification, the softer outer lens cortex is removed with suction. An intraocular lens (IOL) is then introduced into the empty lens capsule restoring the patient's vision.

In some cases, one or more of the large aspirated particle(s) may cause an occlusion in the aspiration line. When the occlusion releases, a traumatic vacuum surge in the aspiration line may result in damage to the patient eye. Several techniques for preventing vacuum surge in various types of medical systems have been published.

For example, U.S. Patent Application Publication No. 2008/0319374 describes a post-occlusion chamber collapse canceling system for a surgical apparatus. The system detects the breaking of occlusions by tissue fragments in the distal end of the aspiration path and produces a response consisting in a transitory blockage of the distal end the aspiration path to terminate the chamber collapse and a transitory venting of the aspiration line to relieve the vacuum, in a way that post-occlusion chamber collapses are cancelled.

U.S. Patent Application Publication No. 2004/0049217 describes a surgical cutting system that includes a cutter which has an inner sleeve that moves adjacent to an aspiration port of an outer sleeve. The inner sleeve is coupled to a source of vacuum that pulls tissue into the outer port when the inner sleeve is moved away from the port. The inner sleeve then moves across the outer port and severs the tissue in a guillotine fashion. The tip of the inner sleeve may exert a spring force that assist in the cutting action of the cutter. The cutter includes a motor which creates an oscillating translational movement of the sleeve. The motor can be controlled by a controller that is coupled a foot pedal. The foot pedal and controller can be configured so that the motor decreases speed as the pedal is depressed by the operator. The inner sleeve is coupled to an aspiration line that pulls the severed tissue out of the cutter. The level of the aspiration vacuum pressure can be controlled by a variable regulator valve. The regulator valve is coupled to the controller and the foot pedal. The foot pedal may have a switch that allows the system to operate in either a variable speed mode or a variable pressure mode. In the variable speed mode the actuation of the foot pedal changes the speed of the motor. In the variable pressure mode the actuation of the foot pedal changes the vacuum level within the aspiration line.

SUMMARY

An embodiment of the present invention that is described herein provides a system including a solenoid valve, which is positioned in the system between (i) a handle of a probe, and (ii) an aspiration line coupled with the handle for aspirating fluids from the probe, a sensor, and a controller. The solenoid valve includes: a valve body including ports including an inlet port and an outlet port, a valve cavity having a direction of elongation and configured to provide fluid connectivity between respective ones of the ports, a solenoid coil disposed in the valve body around the valve cavity, and a plunger including a permanent magnet, and configured to move back-and-forth along the direction of elongation between a first position and a second position in the valve cavity to selectively control the fluid connectivity between respective ones of the ports. The sensor is positioned between the handle and the aspiration line and is configured to produce a signal indicative of a fluid metric in the aspiration line. The controller is configured to identify, based on the signal, a vacuum surge in the aspiration line, and, in response to identifying the vacuum surge, to apply at least one current to the solenoid coil to selectively move the plunger between the first position and the second position, and to selectively maintain the plunger in the first position and the second position.

In some embodiments, the controller is configured to estimate a baseline value of the fluid metric based on the signal, to set a threshold depending on the baseline value of the fluid metric, and to identify the vacuum surge by detecting that the fluid metric crosses the threshold. In other embodiments, the controller is configured to re-estimate the baseline value over time, and to adapt the threshold depending on the re-estimated baseline value. In yet other embodiments, the controller is configured to set one or more additional thresholds indicative of a gradual change in the fluid metric, and to identify a change in a vacuum level in the aspiration line before the vacuum surge by detecting that the fluid metric crosses at least one of the one or more thresholds.

In an embodiment, the valve body includes at least one shock absorber, and the at least one shock absorber is configured to soften striking of the plunger against the valve body in the direction of elongation. In another embodiment, the fluid metric includes a pressure level of the fluid in the aspiration line, and the sensor is configured to measure the pressure level. In yet another embodiment, the fluid metric includes a flow rate of the fluid aspirated in the aspiration line, and the sensor is configured to measure the flow rate.

In some embodiments, in addition to applying the at least one current to the solenoid coil, the controller is configured to apply a corrective action for reducing a vacuum level in the aspiration line. In other embodiments, the controller is configured to reduce the vacuum level by venting the aspiration line. In yet other embodiments, the controller is configured to reduce the vacuum level by controlling a pump for increasing a pressure in the aspiration line.

There is additionally provided, in accordance with an embodiment of the present invention, a method including: in a system having a solenoid valve that includes: (i) a valve body including ports including an inlet port and an outlet port, a valve cavity having a direction of elongation and configured to provide fluid connectivity between respective ones of the ports, (ii) a solenoid coil disposed in the valve body around the valve cavity, and (iii) a plunger including a permanent magnet, and configured to move back-and-forth along the direction of elongation between a first position and a second position in the valve cavity to selectively control the fluid connectivity between respective ones of the ports, receiving a signal indicative of a fluid metric in an aspiration line coupled to a handle of a probe for aspirating fluids from the probe. Based on the signal, a vacuum surge is identified in the aspiration line. In response to identifying the vacuum surge, at least one current is applied to the solenoid coil to selectively move the plunger between the first position and the second position, and to selectively maintain the plunger in the first position and the second position.

There is provided in accordance with an embodiment of the present disclosure, a fluid dynamics system, including a solenoid valve including a valve body including ports including an inlet port and an outlet port, a valve cavity having a direction of elongation and configured to provide fluid connectivity between respective ones of the ports, and at least one shock absorber, a solenoid coil disposed in the valve body around the valve cavity, and a plunger including a permanent magnet, and configured to move back-and-forth along the direction of elongation between a first position and a second position in the valve cavity to selectively control the fluid connectivity between respective ones of the ports, wherein the at least one shock absorber is configured to soften striking of the plunger against the valve body in the direction of elongation, and a controller configured to apply at least one current to the solenoid coil to selectively move the plunger between the first position and the second position, and to selectively maintain the plunger in the first position and the second position.

Further in accordance with an embodiment of the present disclosure the plunger does not have a fixed rest position in the valve cavity.

Still further in accordance with an embodiment of the present disclosure the plunger does not include a restoring element configured to restore the plunger to a fixed rest position.

Additionally, in accordance with an embodiment of the present disclosure the plunger will not remain in the first position and second position without applying the at least one current to the solenoid coil.

Moreover, in accordance with an embodiment of the present disclosure the plunger will remain in the first position or the second position upon application of the at least one current to the solenoid coil.

Further in accordance with an embodiment of the present disclosure the valve body includes a first shock absorber and a second shock absorber configured to soften striking of the plunger against the valve body in the direction of elongation when the plunger strikes the valve body at the first position, and when the plunger strikes the valve body at the second position, respectively.

Still further in accordance with an embodiment of the present disclosure the first shock absorber and the second shock absorber do not include a spring.

Additionally, in accordance with an embodiment of the present disclosure the first shock absorber and the second shock absorber each include resilient material.

Moreover, in accordance with an embodiment of the present disclosure the resilient material includes one or more selected from the group consisting of silicone rubber, synthetic rubber, natural rubber, and polyurethane.

Further in accordance with an embodiment of the present disclosure the first shock absorber and the second shock absorber each include a flat surface facing the plunger.

Still further in accordance with an embodiment of the present disclosure the first shock absorber and the second shock absorber each include a rounded surface facing the plunger.

Additionally, in accordance with an embodiment of the present disclosure the first shock absorber and the second shock absorber each include a conical surface facing the plunger.

Moreover, in accordance with an embodiment of the present disclosure the controller is configured to apply a first current to the solenoid coil to activate the solenoid coil with a first polarity to cause the plunger to move and be maintained in the first position, and apply a second current to the solenoid coil to activate the solenoid coil with a second opposite polarity to cause the plunger to move and be maintained in the second position.

Further in accordance with an embodiment of the present disclosure the permanent magnet has a center with respect to the direction of elongation, the solenoid coil has a center with respect to the direction of elongation, and the valve body further includes a spacer coupled with the first shock absorber, to prevent the center of the magnet from moving in the direction of elongation past the center of the solenoid coil and maintain asymmetry between the center of the solenoid coil and the center of the permanent magnet with respect to the direction of elongation.

Still further in accordance with an embodiment of the present disclosure in the first position of the plunger, the plunger abuts the first shock absorber.

Additionally in accordance with an embodiment of the present disclosure, the system includes a medical tool including the solenoid valve, an irrigation channel, an aspiration channel which traverses the solenoid valve, and a sensor configured to provide a signal indicative of a fluid metric in the aspiration channel, the controller being configured to selectively control the fluid connectivity in the aspiration channel between the inlet port and the outlet port responsively to the fluid metric.

Moreover, in accordance with an embodiment of the present disclosure the fluid metric is a pressure level.

Further in accordance with an embodiment of the present disclosure the controller is configured to detect a rate of change of the fluid metric in the aspiration channel, and reduce the fluid connectivity between the inlet port and the outlet port responsively to the detected rate of change passing a given rate of change.

Still further in accordance with an embodiment of the present disclosure the controller is configured to increase the fluid connectivity between the inlet port and the outlet port responsively to the fluid metric passing a given value.

Additionally, in accordance with an embodiment of the present disclosure the medical tool further includes a probe body including a horn, a needle, a part of the irrigation channel and a section of the aspiration channel, and a fluid dynamics cartridge configured to be reversibly connected to the probe body, and including the sensor and the solenoid valve, which includes another section of the aspiration channel.

Moreover, in accordance with an embodiment of the present disclosure the fluid dynamics cartridge includes the controller.

There is also provided in accordance with another embodiment of the present disclosure, a fluid dynamics system, including a solenoid valve including a valve body including ports including an inlet port and an outlet port, a valve cavity having a direction of elongation and configured to provide fluid connectivity between respective ones of the ports, and at least one shock absorber, a solenoid coil disposed in the valve body around the valve cavity, and a plunger including magnetic material, and configured to move back-and-forth along the direction of elongation between a first position and a second position in the valve cavity to selectively control the fluid connectivity between respective ones of the ports, wherein the at least one shock absorber is configured to soften striking of the plunger against the valve body in the direction of elongation, wherein the at least one shock absorber includes a conical surface facing the plunger.

Further in accordance with an embodiment of the present disclosure the plunger does not have a fixed rest position in the valve cavity.

Still further in accordance with an embodiment of the present disclosure the plunger does not include a restoring element configured to restore the plunger to a fixed rest position.

Additionally, in accordance with an embodiment of the present disclosure the plunger will not remain in the first position and second position without applying at least one current to the solenoid coil.

Moreover, in accordance with an embodiment of the present disclosure the plunger will remain in the first position or the second position upon application of at least one current to the solenoid coil.

Further in accordance with an embodiment of the present disclosure the valve body includes a first shock absorber and a second shock absorber configured to soften striking of the plunger against the valve body in the direction of elongation when the plunger strikes the valve body at the first position, and when the plunger strikes the valve body at the second position, respectively.

Still further in accordance with an embodiment of the present disclosure the first shock absorber and the second shock absorber do not include a spring.

Additionally, in accordance with an embodiment of the present disclosure the first shock absorber and the second shock absorber each include resilient material.

Moreover, in accordance with an embodiment of the present disclosure the resilient material includes one or more selected from the group consisting of silicone rubber, synthetic rubber, natural rubber, and polyurethane.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
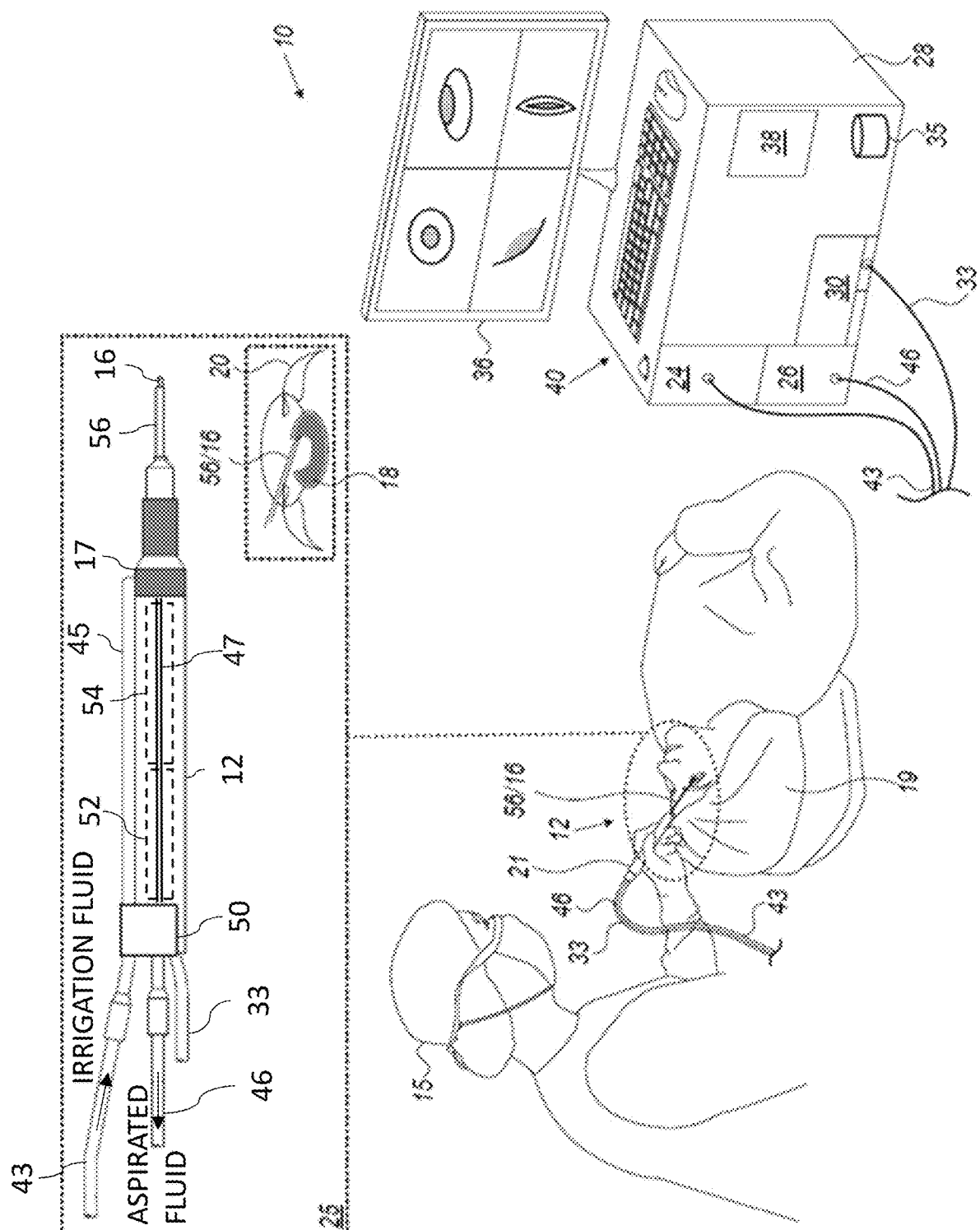
FIG. 1 is a partly pictorial, partly block diagram view of a phacoemulsification system constructed and operative in accordance with an embodiment of the present invention.

During phacoemulsification of an eye lens, the emulsified lens particles are aspirated. When a particle blocks the inlet of an aspiration channel (which could be in a needle of a phacoemulsification probe) causing occlusion of the channel, the vacuum in the channel increases. When the channel becomes unblocked (e.g., by the particle being subsequently sucked down the channel), the high vacuum in the channel causes an aspiration surge known as a post occlusion surge, which may have traumatic consequences to the eye. For example, sensitive parts of the eye may be damaged or come into contact with the needle of the phacoemulsification probe.

A possible solution to the problem of vacuum level surge is incorporating an aspiration bypass. Such a bypass may consist of a small hole or channel between an irrigation channel of the probe and the aspiration channel. When a blockage occurs, the high vacuum diverts irrigation fluid into the aspiration channel via the hole, thereby limiting the vacuum level.

However, the above-described bypass aspiration technique is still prone to produce a traumatic aspiration surge when the channel unblocks, since the high vacuum is present in a long tube (which being flexible may also be compressed adding to the vacuum problem) between a portion of the aspiration channel inside the emulsification probe and the aspiration pump, and that large, partially vacant volume, may therefore cause a surge when the occlusion breaks. Moreover, diversion of irrigation fluid may cause an uncontrolled pressure-drop in the irrigation channel, which may also pose a risk to the eye.

Embodiments of the present invention generally solve the above problems by removing or reducing the pressure difference in the aspiration channel during the occlusion clearance. Embodiments of the present invention control fluid connectivity in the aspiration channel during occlusion clearance using an extremely fast-acting and programmable solenoid valve. The solenoid valve includes a solenoid coil which moves a plunger including a permanent magnet in a valve cavity. Two parts of the aspiration channel are connected to the valve cavity via ports in the valve cavity. Therefore, movement of the plunger in the valve cavity controls the fluid connectivity in the aspiration channel.

In some embodiments, the permanent magnet may be replaced by any suitable magnetic material, which is subjected to a force in a magnetic field, for example, but not limited to, iron, cobalt, nickel, gadolinium, and/or neodymium.

The solenoid valve does not need a restoring element (such as a spring) to keep the plunger in a rest position when a current is not applied to the solenoid coil. An electric current needs to be applied to the solenoid coil to selectively open the valve and keep the valve open, and to close the valve and keep the valve closed. If a current is not supplied to the solenoid coil, the position of the plunger may be unstable and unknown. Using a solenoid valve without a restoring element allows the plunger to be moved quickly with a selected force, while minimizing electrical power needed to open or close the valve thereby reducing heat generated by the solenoid valve. The solenoid valve is opened and closed by changing the polarity of the solenoid coil by changing the direction of the current applied to the solenoid coil.

In some embodiments, a spacer is placed in the path of the plunger preventing a center of the permanent magnet of the plunger (with respect to a direction of elongation of the valve cavity) from being aligned with a center of the solenoid coil (with respect to a direction of elongation of the valve cavity). In this asymmetrical state, the permanent magnet is not subjected to unstable forces from the solenoid coil and the plunger can be moved from one position to another by changing the polarity of the solenoid coil thereby providing a quick and effective opening and closing of the solenoid valve.

As the opening and closing of the solenoid valve is performed quickly and sometimes the solenoid valve is repeatedly opened and closed many times a second, the plunger may strike against a body of the valve causing a loud noise and vibration of a medical tool (such as a phacoemulsification probe) in which the valve is operating. The noise and vibration are disturbing for the physician operating the tool as well as making it difficult for the physician to steadily hold the tool. Therefore, in some embodiments, the solenoid valve includes one or more shock absorbers to soften the striking of the plunger against the valve body in the direction of elongation. The solenoid valve may include two shock absorbers placed at either end of the valve cavity to soften the striking of the plunger against the valve body as the plunger moves from one extreme to another within the valve cavity. The shock absorbers do not typically include springs. The shock absorbers are generally formed from a resilient material such as silicone rubber, natural rubber, synthetic rubber, or polyurethane. The shock absorbers may have any suitable shape. The shock absorbers include a surface which faces the plunger in use. This surface may have any suitable shape, for example, a flat surface, a rounded surface, or a conical surface.

In some embodiments, a sensor (e.g., pressure sensor, flow sensor, or any suitable sensor) connected to or coupled with the aspiration channel provides a signal indicative of a fluid metric (e.g., pressure level, or flow rate of the aspirated fluid) in the aspiration channel and a controller selectively controls fluid connectivity along the aspiration channel by applying a suitable current to the solenoid coil to selectively open or close the solenoid valve. In some embodiments, when the controller detects a rate of change in the fluid metric (e.g., pressure level, or flow rate of the aspirated fluid) in the aspiration channel passing (e.g., exceeding) a given rate of change, which is indicative of an occlusion breaking, the controller reduces fluid connectivity in the aspiration channel by closing the solenoid valve quickly (for example, in 10 milliseconds or less) thereby isolating the eye from the vacuum created in a majority of the aspiration channel and/or aspiration line until the pressure in the aspiration channel and/or aspiration line returns to a desired and/or safe pressure. The pressure in the aspiration channel may be changed, in a non-time critical manner, by adjusting or stopping an aspiration pump acting on the aspiration channel and/or by externally venting the aspiration line, and/or any other suitable method. Once the fluid metric (e.g., pressure level, or flow rate of the aspirated fluid) in the aspiration channel passes a given value (e.g., given pressure level), the controller reopens the solenoid valve without causing a vacuum surge which could damage the eye.

In some embodiments, in addition to being linear, the solenoid valve is small and may be produced at low-cost thereby allowing the valve to be disposed of after use. Therefore, in some embodiments, the valve does not need to withstand repeated sterilization. The valve may be housed in a cartridge which is reversibly connected to the phacoemulsification probe and aspiration and irrigation tubes. The cartridge may then be removed from the probe and tubes after use for cleaning or disposal.

In some embodiments, sensors (e.g., a pressure sensor for the aspiration channel and a pressure sensor for the irrigation channel) may be included in the cartridge). Including the sensors in the cartridge may provide higher sensitivity to local changes in fluid dynamics and provide a higher degree of control of the pressure in the eye.

In some embodiments, the controller is also included in the cartridge. Including the controller in the cartridge may allow the controller to be configured for the calibration of the solenoid valve. Additionally, or alternatively, including the controller in the cartridge allows the controller to be close to the sensor or sensors which may be providing analog signals that could degrade if the signals needed to travel over a cable to a remote console in which the controller may otherwise be installed.

System Description

Reference is now made to FIG. 1 is a partly pictorial, partly block diagram view of a phacoemulsification system 10 constructed and operative in accordance with an embodiment of the present invention.

The phacoemulsification system 10 comprises a phacoemulsification probe 12 (e.g., handpiece). In some embodiments, the phacoemulsification probe 12 may be replaced by any suitable medical tool. As seen in the pictorial view of phacoemulsification system 10, and in inset 25, phacoemulsification probe 12 comprises a needle 16, a probe body 17, and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, irrigation sleeve 56 may have one or more side ports at, or near, the distal end to allow irrigation fluid to flow towards the distal end of the phacoemulsification probe 12 through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, Calif., USA.

In the embodiment of FIG. 1, during the phacoemulsification procedure, a pumping sub-system 24 comprised in a console 28 pumps irrigation fluid from an irrigation reservoir (not shown) to the irrigation sleeve 56 to irrigate the eye 20. The irrigation fluid is pumped via an irrigation tubing line 43 running from the console 28 to an irrigation channel 45 of probe 12, the distal end of the irrigation channel 45 including the fluid pathway in the irrigation sleeve 56. The irrigation tubing line 43 is typically flexible and may be prone to collapsing during an occlusion of the needle 16. In another embodiment, the pumping sub-system 24 may be coupled or replaced with a gravity fed irrigation source such as a balanced salt solution (BSS) bottle/bag.

Eye fluid and waste matter (e.g., emulsified parts of the cataract) are aspirated via an aspiration channel 47, which extends from the hollow of needle 16 through the phacoemulsification probe 12, and then via an aspiration tubing line 46 to a collection receptacle in the console 28. The aspiration is affected by a pumping sub-system 26, also comprised in console 28.

System 10 may include a fluid dynamics cartridge 50 (which in an embodiment, may be removable), which may include one or more valves to regulate the flow of fluid in the irrigation channel 45 and/or aspiration channel 47 as well as sensors, described in more detail with reference to FIGS. 2A-6. Part of the irrigation channel 45 and the aspiration channel 47 is disposed in the probe body 17 and part is disposed in the cartridge 50.

Phacoemulsification probe 12 includes other elements, such as a piezoelectric crystal 52 coupled to a horn 54 to drive vibration of needle 16. The piezoelectric crystal is configured to vibrate needle 16 in a resonant vibration mode. The vibration of needle 16 is used to break a cataract into small pieces during a phacoemulsification procedure. Console 28 comprises a piezoelectric drive module 30, coupled with the piezoelectric crystal 52, using electrical wiring running in a cable 33. Drive module 30 is controlled by a controller 38 and conveys processor-controlled driving signals via cable 33 to, for example, maintain needle 16 at maximal vibration amplitude. The drive module may be realized in hardware or software, for example, in a proportional-integral-derivative (PID) control architecture. The controller 38 may also be configured to receive signals from sensors in the phacoemulsification probe 12 and control one or more valves to regulate the flow of fluid in the irrigation channel 45 and/or the aspiration channel 47, as described in more detail with reference to FIG. 6. In some embodiments, at least some of the functionality of the controller 38 may be implemented using a controller disposed in the phacoemulsification probe 12 (e.g., the cartridge 50).

Controller 38 may receive user-based commands via a user interface 40, which may include setting a vibration mode and/or frequency of the piezoelectric crystal 52, and setting or adjusting an irrigation and/or aspiration rate of the pumping sub-systems 24/26. In some embodiments, user interface 40 and a display 36 may be combined as a single touch screen graphical user interface. In some embodiments, the physician 15 uses a foot pedal (not shown) as a means of control. Additionally, or alternatively, controller 38 may receive the user-based commands from controls located in a handle 21 of probe 12.

Some or all of the functions of controller 38 may be combined in a single physical component or, alternatively, implemented using multiple physical components. These physical components may comprise hard-wired or programmable devices, or a combination of the two. In some embodiments, at least some of the functions of controller 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system shown in FIG. 1 may include further elements which are omitted for clarity of presentation. For example, physician 15 typically performs the procedure using a stereo microscope or magnifying glasses, neither of which are shown. Physician 15 may use other surgical tools in addition to probe 12, which are also not shown in order to maintain clarity and simplicity of presentation.

Figures 2A, 2B:
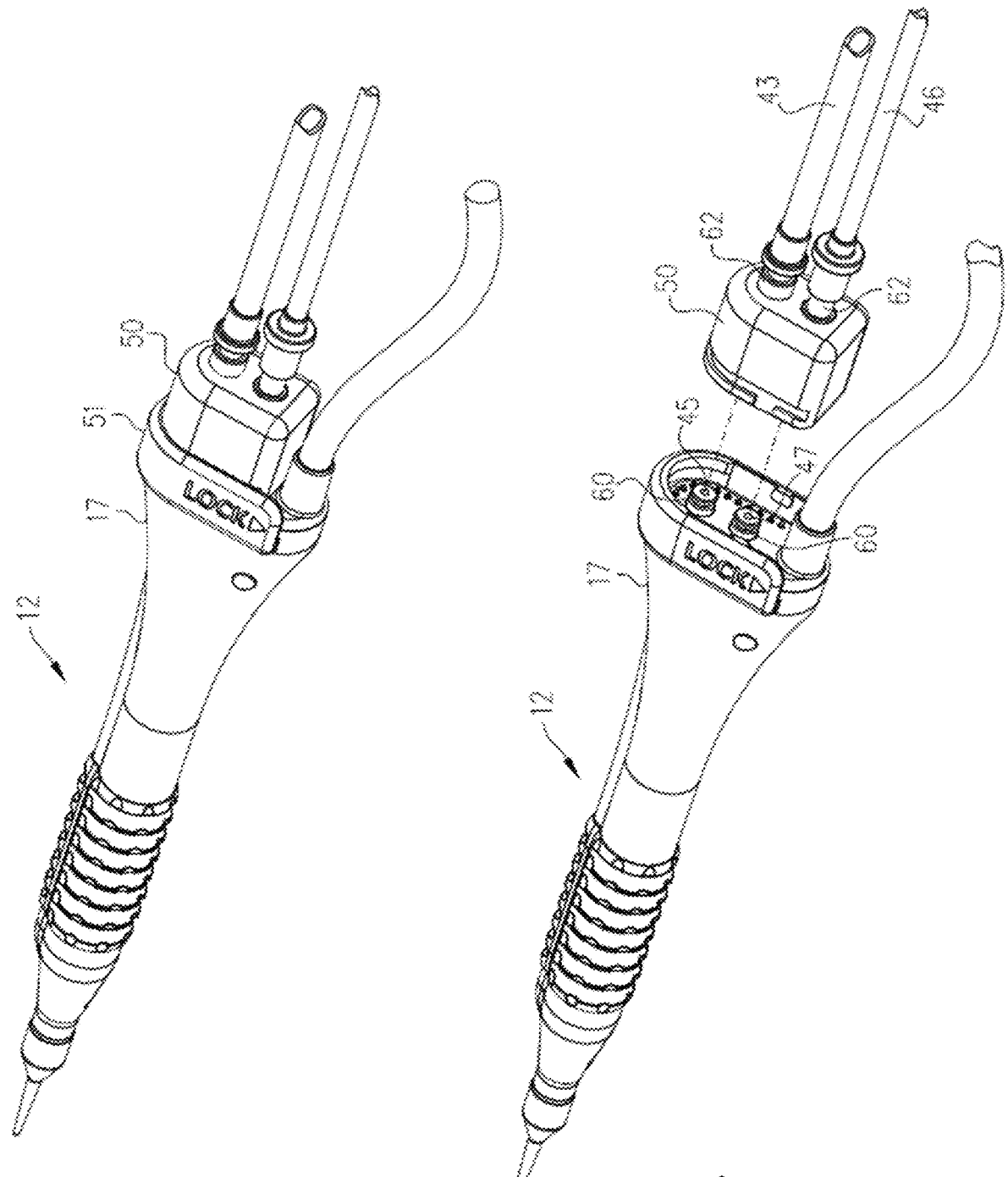
FIGS. 2A-B are views of a probe for use with the system of FIG. 1, in accordance with embodiments of the present invention.

Reference is now made to FIGS. 2A-B, which are views of the phacoemulsification probe 12 for use with the system 10 of FIG. 1. FIG. 2A shows the cartridge 50, which is configured to be reversibly attached (using a clip 51) to the probe body 17 of the phacoemulsification probe 12. FIG. 2B shows the cartridge 50 detached from the probe body 17. FIG. 2B shows ports 60 of the irrigation channel 45 and the aspiration channel 47 on the probe body 17 for connecting with corresponding ports (not shown in FIG. 2B, but shown in FIG. 3A) of the cartridge 50. FIG. 2B also shows irrigation tubing line 43 and aspiration tubing line 46 connected to ports 62 of the cartridge 50.

Figure 3A:
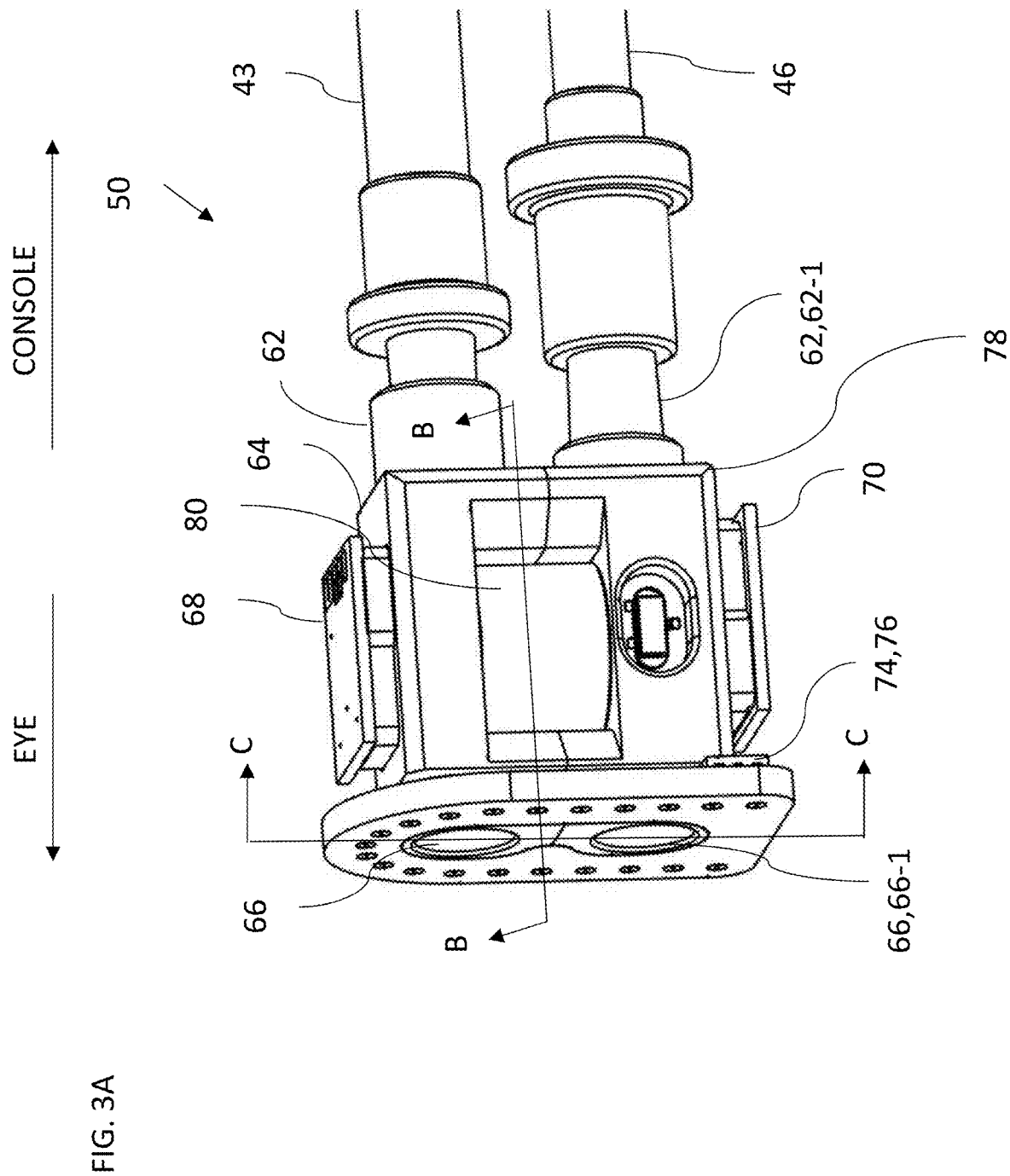
FIG. 3A is a schematic view of an interior of a fluid dynamics cartridge for use in the probe of FIGS. 2A-B, in accordance with an embodiment of the present invention.
Figure 3B:
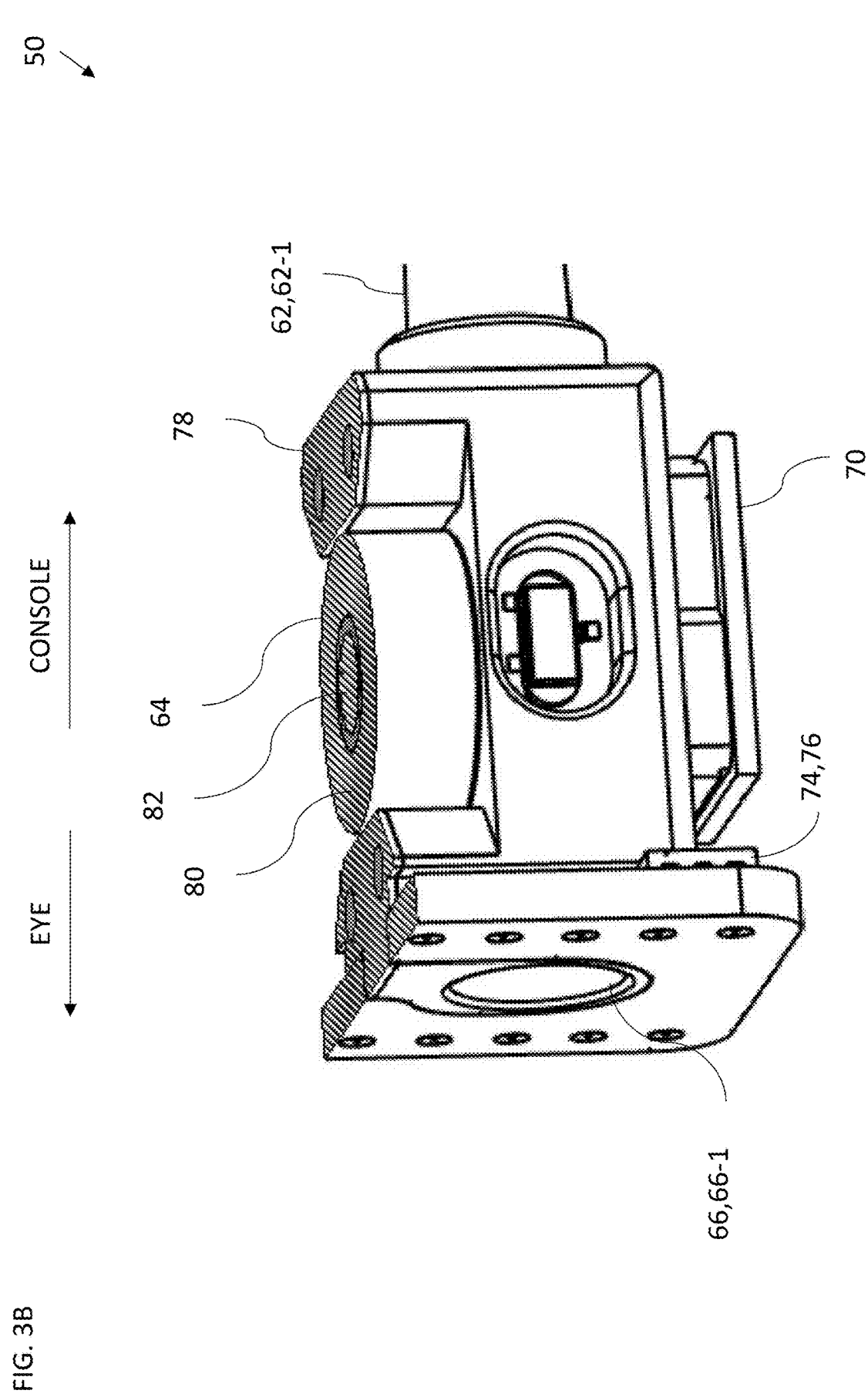
FIG. 3B is a cross-section of the fluid dynamics cartridge through line B:B of FIG. 3A, in accordance with an embodiment of the present invention.
Figure 3C:
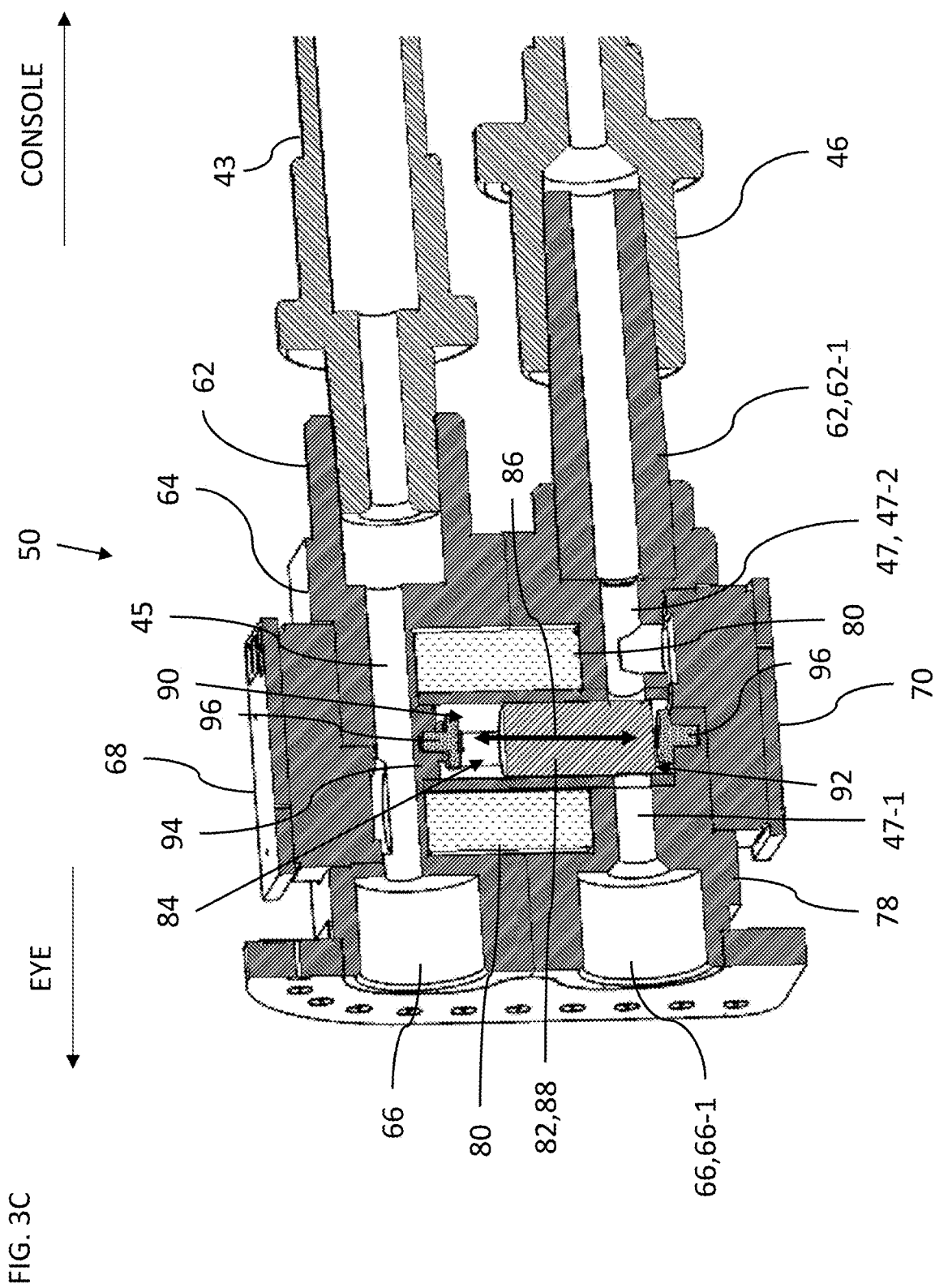
FIG. 3C is a cross-section of the fluid dynamics cartridge through line C:C of FIG. 3A, in accordance with an embodiment of the present invention.

Reference is now made to FIGS. 3A-C. FIG. 3A is a schematic view of an interior of a fluid dynamics cartridge 50 for use in the phacoemulsification probe 12 of FIGS. 2A-B. FIG. 3B is a cross-section of the fluid dynamics cartridge 50 through line B:B of FIG. 3A. FIG. 3C is a cross-section of the fluid dynamics cartridge 50 through line C:C of FIG. 3A.

The phacoemulsification probe 12 may include sensors 68, and 70 (which may be pressure sensors), and a solenoid valve 64. In some embodiments, the cartridge 50 includes: the solenoid valve 64, which includes ports 62 for connection to the irrigation tubing line 43 and aspiration tubing line 46, ports 66 for connection to the ports 60 (FIG. 2B), and sections of the irrigation channel 45 and aspiration channel 47; the sensor 68 connected to the irrigation channel 45; and the sensor 70 connected to aspiration channel 47 on the console 28 side of the solenoid valve 64 (as shown in FIG. 3C). The sensor 68 and the sensor 70 are configured to provide respective signals indicative of respective fluid metrics (e.g., pressure levels, or flow rate of the aspirated fluid) in the irrigation channel 45 and in the aspiration channel 47. The aspiration channel 47 traverses the solenoid valve 64.

Including the sensors 68, 70 in the cartridge 50 may provide higher sensitivity to local changes in fluid dynamics and provide a higher degree of control of the pressure in the eye.

The phacoemulsification probe 12 may include a controller 74 to receive the signal(s) from the pressure sensor 68 and/or the pressure sensor 70, and control the fluid connectivity in the irrigation channel 45 and/or the aspiration channel 47 by selectively opening and closing the solenoid valve 64, responsively to the received signal(s). In some embodiments, the cartridge 50 may also include the controller 74 and/or a memory 76 (e.g., EEPROM) to hold calibration settings and/or a usage counter to count usage of the cartridge 50 and thereby prevent overuse of the cartridge 50. In some embodiments, the controller 74 may be included in the console 28 (FIG. 1). In some embodiments, the functionality of the controller 74 may be performed by the controller 38. Including the controller 74 in the cartridge 50 may allow the controller to be configured for the calibration of the solenoid valve 64. Additionally, or alternatively, including the controller 74 in the cartridge 50 allows the controller to be close to the sensors 68, 70 which may be providing analog signals that could degrade if the signals needed to travel over the cable 33 to the console 28 in which the controller 74 may otherwise be installed.

In some embodiments, solenoid valve 64 is positioned between handle 21 of probe 12 and aspiration tubing line 46, also referred to herein as "an aspiration line," for brevity. In the present example, solenoid valve 64 is coupled with handle 21 for controlling aspirating fluid(s) from aspiration channel 47 of probe 12.

In some embodiments, sensor 70 is positioned between handle 21 and aspiration tubing line 46 and is configured to produce a signal indicative of a fluid metric (e.g., pressure level, or flow rate of the aspirated fluid) both in aspiration channel 47 and in aspiration tubing line 46.

The cartridge 50 is compact and may be any suitable size. In some embodiments, the cartridge 50 may fit into a cube of 2.5 cm sides.

The aspiration channel 47 includes a section 47-1 coupled to an inlet port 66-1 and a section 47-2 coupled to an outlet port 62-1 (as shown in FIG. 3C). The controller 74 is configured to control the fluid connectivity in the aspiration channel 47 between the inlet port 66-1 and the outlet port 62-1 by selectively opening and closing the solenoid valve 64, responsively to the fluid metric (e.g., pressure level, or flow rate of the aspirated fluid) in the aspiration channel 47. It should be noted that when the solenoid valve 64 is closed, the sensor 70 shown in FIG. 3C is configured to sense a fluid metric (e.g., pressure level, or flow rate of the aspirated fluid) in the section 47-2 between the solenoid valve 64 and the console 28.

The solenoid valve 64 and its operation is now described in more detail. The solenoid valve 64 includes a valve body 78, a solenoid coil 80, and a plunger 82.

Reference is now made to FIG. 3C. The valve body 78 includes the ports 62, the ports 66, a valve cavity 84 having a direction of elongation 86 and configured to provide fluid connectivity between respective ones of the ports 62, 66 (e.g., between the inlet port 66-1 and outlet port 62-1). The solenoid coil 80 is disposed in the valve body 78 around valve cavity 84. The plunger 82 includes a permanent magnet 88. The permanent magnet 88 may comprise all of, or only part of, the plunger 82. For example, the plunger 82 may include the permanent magnet 88 coated or covered with a material of low friction. The plunger 82 is configured to move back-and-forth along the direction of elongation 86 between a position 90 and a position 92 in the valve cavity 84 selectively controlling the fluid connectivity between respective ones of the ports 62, 66 (e.g., between the inlet port 66-1 and outlet port 62-1). In some embodiments, the permanent magnet 88 may be replaced by any suitable magnetic material, which is subjected to a force in a magnetic field, for example, but not limited to, iron, cobalt, nickel, gadolinium, and/or neodymium.

The plunger 82 may have any suitable size, for example, a length in the range of 3 mm to 2 cm (e.g., 6 mm) and a diameter in the range of 1 mm to 1 cm (e.g., 3 mm). The valve body 78 may include a spacer 94 described in more detail with reference to FIGS. 5A-B below.

As the opening and closing of the solenoid valve 64 is performed quickly and sometimes the solenoid valve 64 is repeatedly opened and closed many times a second (as described in more detail with reference to FIG. 6), the plunger 82 may strike against the valve body 78 causing a loud noise and vibration of the phacoemulsification probe 12. The noise and vibration are disturbing for the physician 15 (FIG. 1) operating the phacoemulsification probe 12 as well as making it difficult for the physician 15 to steadily hold the phacoemulsification probe 12. Therefore, the solenoid valve 64 includes one or more shock absorbers 96 configured to soften the striking of the plunger 82 against the valve body 78 in the direction of elongation 86. The solenoid valve may include two shock absorbers 96 (as shown in FIG. 3C) placed at either end of the valve cavity 84 configured to soften the striking of the plunger 82 against the valve body 78 as the plunger 82 moves in the direction of elongation 86 from one extreme of the valve body 78 to another (e.g., from position 90 to position 92, and vice-versa) within the valve cavity 84. The shock absorbers 96 do not typically include springs. The shock absorbers 96 generally comprise, or are generally formed from, a resilient material such as silicone rubber, natural rubber, synthetic rubber, or polyurethane. In FIG. 3C, the upper shock absorber 96 forms part of the spacer 94.

In some embodiments, controller 74 is configured to identify, based on the signal received from sensor 70, a vacuum surge (i.e., a sudden drop in pressure) in aspiration channel 47 and aspiration tubing line 46. In response to identifying the vacuum surge, controller 74 (FIGS. 3A-B) is configured to apply at least one current to the solenoid coil 80 to selectively move the plunger 82 between the position 90 and the position 92, and to selectively maintain the plunger in the position 90 and the position 92, as described below in more detail with reference to FIGS. 5A-B.

In other embodiments, controller 74 is configured to (i) estimate a baseline value of the fluid metric (e.g., pressure or flow rate) based on the signal received from sensor 70, (ii) set a threshold depending on the baseline value of the fluid metric, and (iii) identify the vacuum surge by detecting that the fluid metric crosses the threshold. Moreover, controller 74 is configured to re-estimate the baseline value over time, and to adapt the threshold depending on the re-estimated baseline value. These embodiments are described in detail in FIG. 7 below.

In some cases, the vacuum increase may be gradual (e.g., when the inner diameter of the tip of needle 16 is partially closed). In some embodiments, controller 74 is configured to set, in addition to the threshold depending on the baseline value of the fluid metric, one or more additional thresholds in order to identify the gradual increase in vacuum (i.e., gradual drop in pressure). In such embodiments, controller 74 is configured to carry out a corrective action for adjusting the vacuum-level of the fluid aspiration in aspiration tubing line 46 and/or aspiration channel 47, for example, by adjusting the current applied to solenoid valve 64.

Figure 3G:
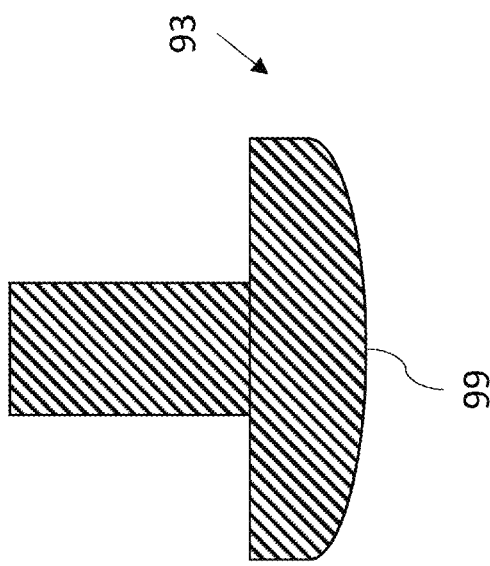
FIGS. 3F-G are cross-sectional views of alternative shock absorbers for use in the cartridge of FIG. 3C, in accordance with embodiments of the present invention.
Figure 3F:
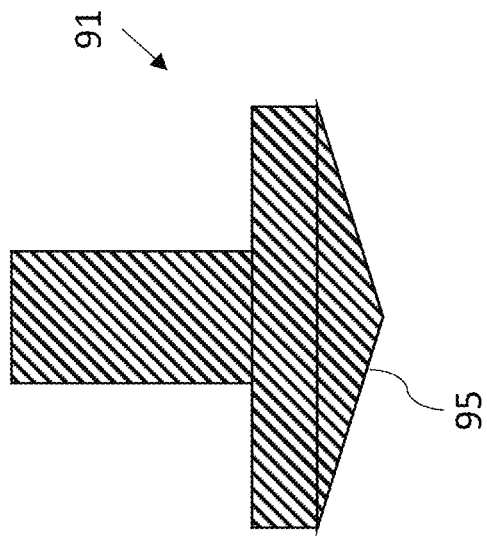
Figure 3E:
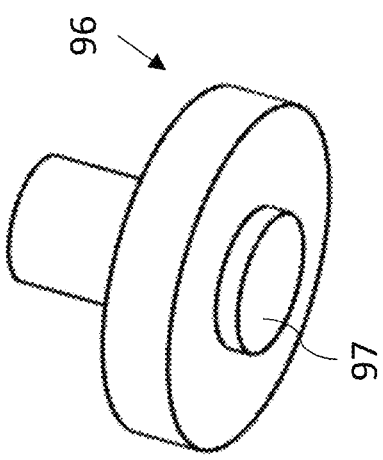
FIGS. 3D-E are schematic views of a shock absorber for use in the cartridge of FIG. 3C, in accordance with embodiments of the present invention.
Figure 3D:
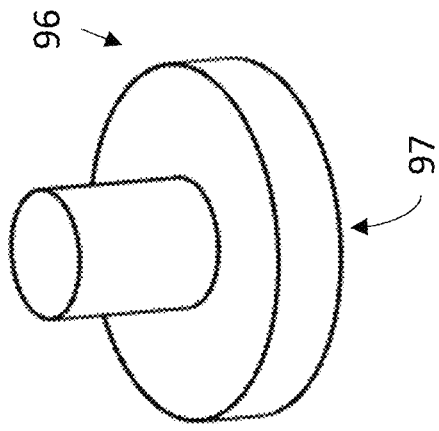

Reference is now made to FIGS. 3D-E, which are schematic views of the shock absorber 96 for use in the cartridge 50 of FIG. 3C. Each shock absorber 96 includes a flat surface 97 facing the plunger 82 (FIG. 3C).

Reference is now made to FIGS. 3F-G, which are cross-sectional views of alternative shock absorbers 91, 93 for use in the cartridge 50 of FIG. 3C. Two shock absorbers 91 or two shock absorber 93 (or any suitable combination) may be used in the solenoid valve 64 instead of the shock absorbers 96. The shock absorber 91 of FIG. 3F includes a conical surface 95 facing the plunger 82. The shock absorber 93 of FIG. 3G includes a rounded surface 99 facing the plunger 82.

Figure 4B:
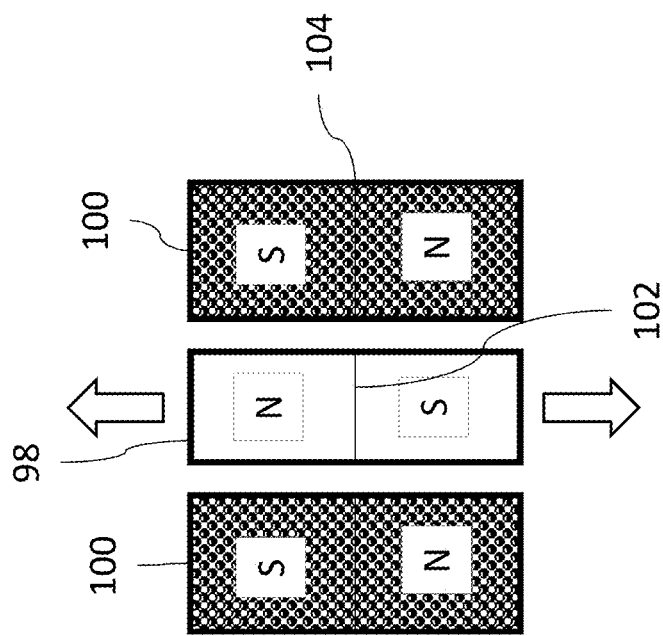
FIGS. 4A-B are schematic views of a permanent magnet in a solenoid coil, in accordance with embodiments of the present invention.
Figure 4A:
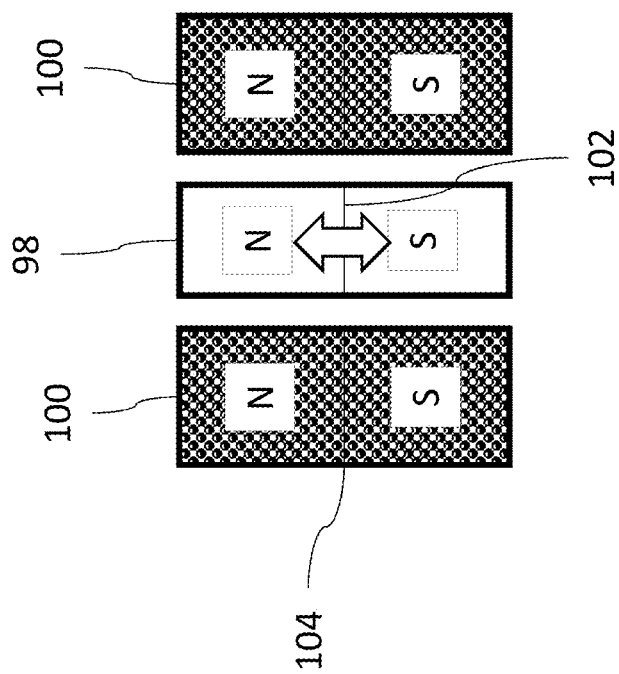

Reference is now made to FIGS. 4A-B, which are schematic views of a permanent magnet 98 in a solenoid coil 100.

In the configuration of FIG. 4A, the polarity of the solenoid coil 100 is in the same direction as the polarity of the permanent magnet 98. In such a configuration, if a center 102 of the permanent magnet 98 is moved a little away from a center 104 of the solenoid coil 100, the permanent magnet 98 will oscillate around the center 104 of the solenoid coil 100 until the permanent magnet 98 settles so that the center 102 of the permanent magnet 98 is aligned with the center 104 of the solenoid coil 100. The permanent magnet 98 therefore rests in a stable position with respect to the solenoid coil 100.

In the configuration of FIG. 4B, the polarity of the solenoid coil 100 is in the opposite direction to the polarity of the permanent magnet 98. In such a configuration, if the center 102 of the permanent magnet 98 is moved a little away from the center 104 of the solenoid coil 100, the permanent magnet 98 will continue to move in that direction. The permanent magnet 98 in FIG. 4B is therefore in an unstable position with respect to the solenoid coil 100.

Figure 5B:
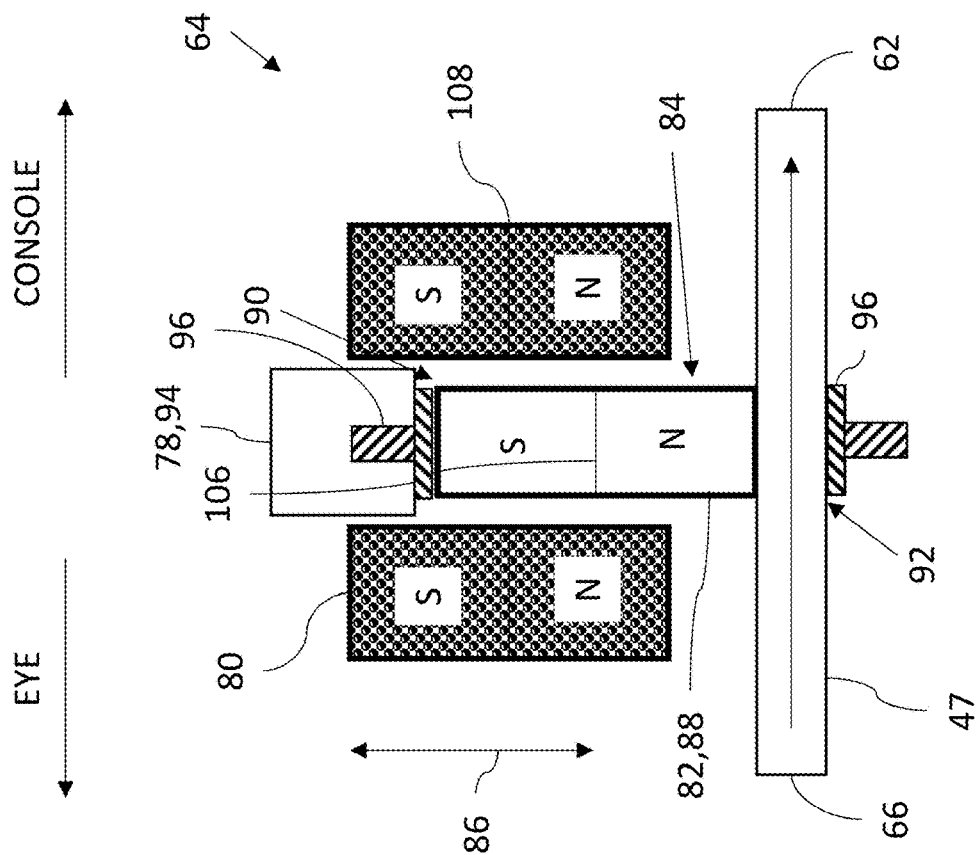
FIGS. 5A-B are schematic views of operation of a solenoid valve for use in the cartridge of FIGS. 3A-C, in accordance with embodiments of the present invention.
Figure 5A:
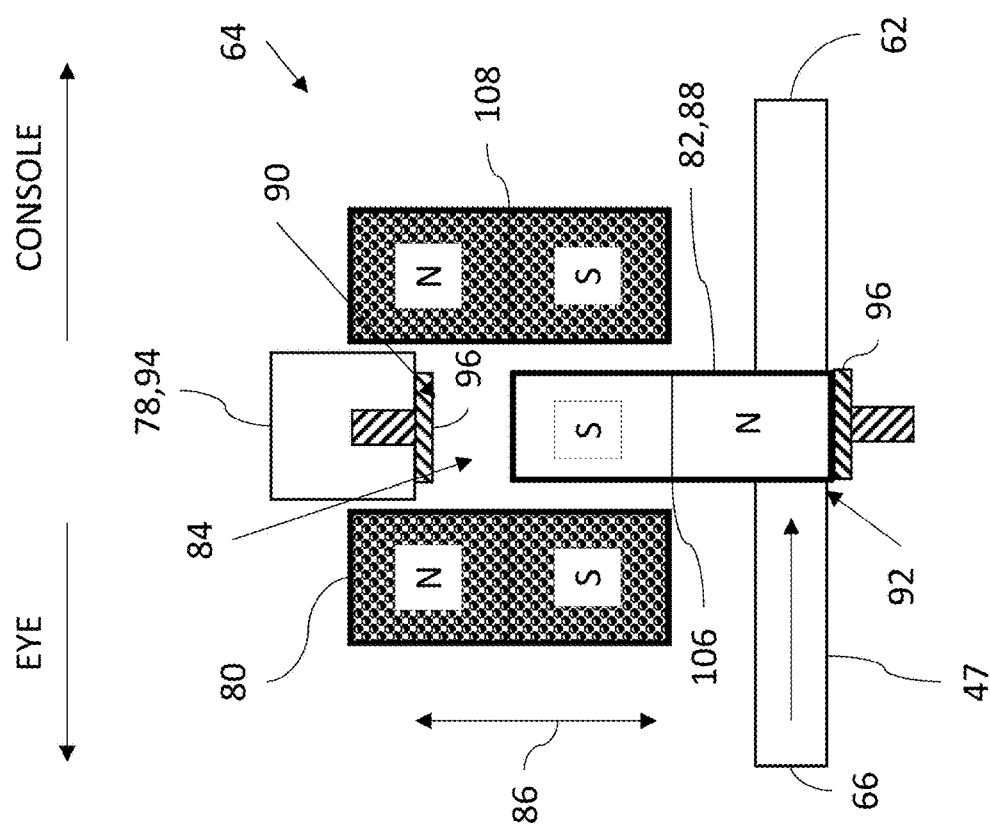

Reference is now made to FIGS. 5A-B, which are schematic views of operation of the solenoid valve 64 for use in the cartridge 50 of FIGS. 3A-C.

The plunger 82 is configured to move back-and-forth along the direction of elongation 86 between position 92 and position 90 in the valve cavity 84 selectively controlling the fluid connectivity between respective ones of the ports 66, 62. The controller 74 (FIGS. 3A-B) is configured to apply current to the solenoid coil 80 to selectively move the plunger 82 between the position 92 and position 90, and to selectively maintain the plunger in the position 92 and position 90. FIG. 5A shows the plunger 82 in position 92 blocking fluid connectivity in the aspiration channel 47. FIG. 5B shows the plunger 82 in position 90 allowing fluid connectivity in the aspiration channel 47.

The plunger 82 does not have a fixed rest position in the valve cavity 84. Even though in some orientations the plunger 82 may fall in one of the positions 92, 94 due to gravity, if the solenoid valve 64 is orientated differently the plunger 84 may fall to a different position. The plunger 82 does not include a restoring element (e.g., spring) configured to restore the plunger 82 to a fixed rest position. The plunger will not always remain in the position 92 or position 90 (e.g., if the orientation of the phacoemulsification probe 12 is changed) without applying current to the solenoid coil 80. In other words, for the solenoid valve 64 to function correctly, a current is applied to the solenoid coil 80 whether the solenoid valve 64 is to remain open or closed. The plunger 82 will remain in the position 90 or the position 92 upon application of current to the solenoid coil 80.

The controller 74 is configured to apply a current to the solenoid coil 80 to activate the solenoid coil 80 with a polarity to cause the plunger 82 to move and be maintained in the position 92 as shown in FIG. 5A. The controller 74 is configured to apply an opposite current to the solenoid coil 80 to activate the solenoid coil 80 with an opposite polarity to cause the plunger 82 to move and be maintained in the position 90 as shown in FIG. 5B.

The permanent magnet 88 has a center 106 with respect to the direction of elongation 86. The solenoid coil 80 has a center 108 with respect to the direction of elongation 86.

The valve body 78 includes the spacer 94 to prevent the center 106 of the magnet 88 moving in the direction of elongation 86 past the center 108 of the solenoid coil 80. Therefore, the spacer 94 maintains asymmetry between the center 108 of the solenoid coil 80 and the center 106 of the permanent magnet 88 with respect to the direction of elongation 86 so that the centers 106, 108 are never aligned with respect to the direction of elongation 86. The above asymmetry is desirable to allow movement of the permanent magnet 88 within the valve cavity 84 to be controlled and the maintained position of the permanent magnet 88 at the position 90 to be stable (as explained above with reference to FIGS. 4A-B). When plunger 82 is in position 90, plunger 82 abuts spacer 94 (see FIG. 5B).

The spacer 94 includes the upper shock absorber 96. When plunger 82 is in position 92, plunger 82 abuts the lower shock absorber 96, and when plunger 82 is in position 90, plunger 82 abuts the upper shock absorber 96. The upper and lower shock absorbers 96 are configured to soften striking of the plunger 82 against the valve body 78 in the direction of elongation 86 when the plunger 82 strikes the valve body 78 at position 90, and when the plunger 82 strikes the valve body 78 at position 92, respectively.

Figure 6:
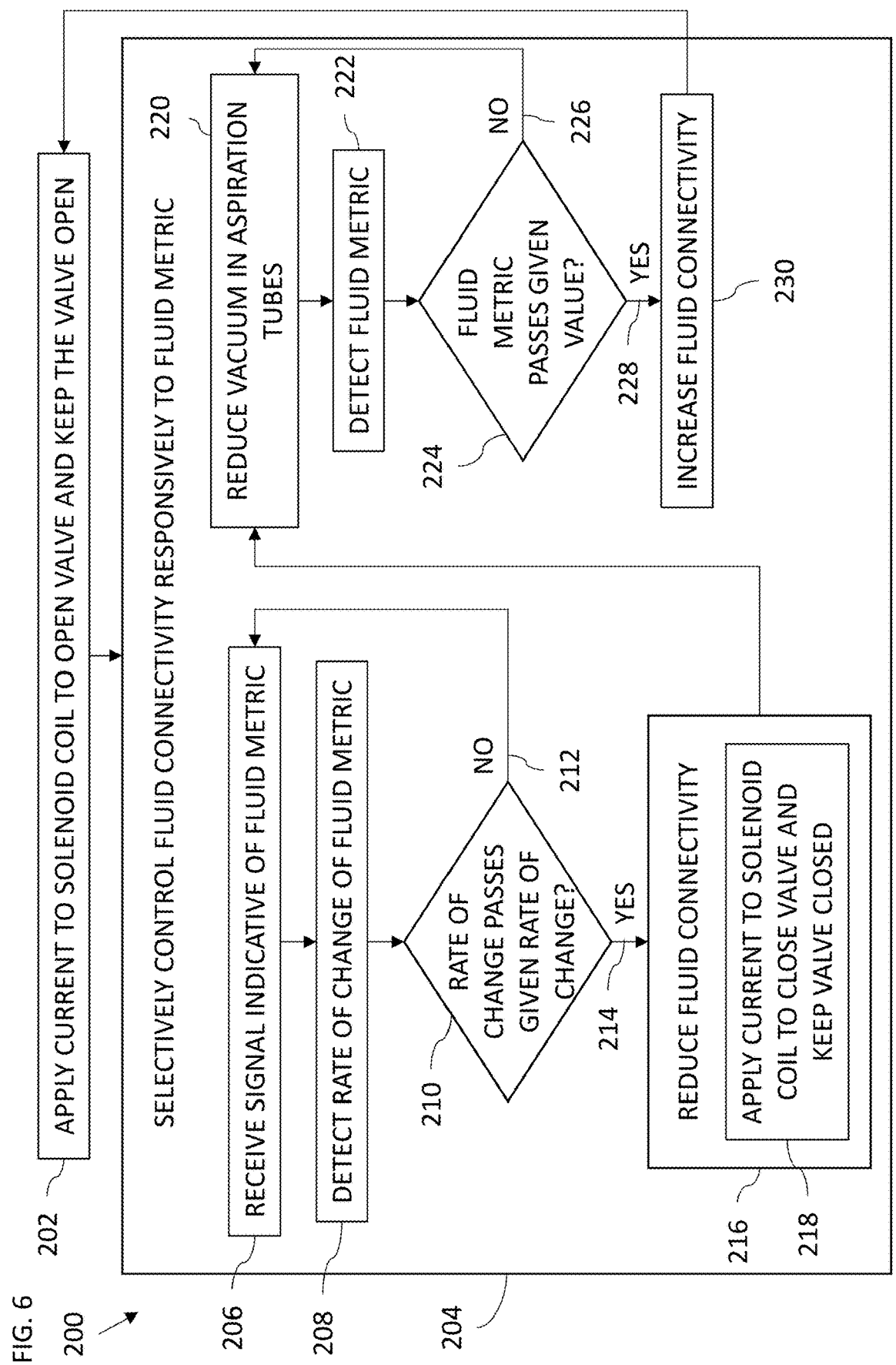
FIG. 6 is a flowchart including steps in a method of operation of system of FIG. 1, in accordance with an embodiment of the present invention.

Reference is now made to FIG. 6, which is a flowchart 200 including steps in an exemplary method of operation of system 10 of FIG. 1. Reference is also made to FIG. 3C.

The controller 74 is configured to apply (block 202) a current to the solenoid coil 80 to activate the solenoid coil 80 with a polarity to cause the plunger 82 to move and be maintained in the position 90 so that the solenoid valve 64 is open (and kept open) and there is fluid connectivity along the aspiration channel 47.

The controller 74 is configured to selectively control (block 204) the fluid connectivity responsively to a measured fluid metric (e.g., a sensed fluid flow or pressure level) in the phacoemulsification probe 12. In some embodiments, the controller 74 is configured to selectively control the fluid connectivity responsively to the fluid metric from the one or more sensors 68, 70 coupled with aspiration channel 47. In this embodiment, the sensor(s) detect a change in pressure, but this method is applicable to other types of sensors known in the art. The step of block 204 is now described in more detail with reference to sub-steps of blocks 206-230.

The controller 74 is configured to receive a signal indicative of the fluid metric (e.g., pressure level, or flow rate of the aspirated fluid) in the aspiration channel 47 from the sensor 70 (block 206). The controller 74 is configured to detect a rate of change of the fluid metric (e.g., pressure level, or flow rate of the aspirated fluid) in the aspiration channel 47 responsively to the received signal (block 208). At a decision block 210, the controller 74 is configured to determine if the rate of change passes (e.g., exceeds) a given rate of change. If the rate of change does not pass (e.g., exceed) the given rate of change (branch 212), the method returns to the sub-step of block 206. If the rate of change passes (e.g., exceeds) the given rate of change (branch 214), the controller 74 is configured to reduce the fluid connectivity (block 216) between the inlet port 66-1 and the outlet port 62-1. The sub-step of block 216 may include the controller 74 being configured to apply a current to the solenoid coil 80 to activate the solenoid coil 80 with an opposite polarity to cause the plunger 82 to move and be maintained in the position 92 (block 218). The solenoid valve 64 is closed and kept closed thereby blocking fluid connectivity in the aspiration channel 47 at the location of the plunger 82 thereby isolating the eye from the aspiration tubing line 46 (FIG. 1) and protecting the eye from a vacuum surge.

In some embodiments, rather than the solenoid valve 64 closing completely and fast, the solenoid valve 64 may be controlled to close partially and/or slowly. In some embodiments, the activation of the solenoid valve 64 may also be controlled according to pressure, flow, temperature, or a combination of these type of sensed parameters.

The controller 74 is configured to reduce the vacuum in the aspiration tubing line 46 (block 220) (and the portion of the aspiration channel 47 between the solenoid valve 64 and the aspiration tubing line 46), for example, by reducing the action of the pumping sub-system 26, or opening a vent in the aspiration tubing line 46 or in the aspiration channel 47. The controller 74 is configured to detect the fluid metric (e.g., pressure level, or flow rate of the aspirated fluid) in the aspiration channel 47 responsively to signal received from the sensor 70 (block 222). At a decision block 224, the controller 74 is configured to determine if the fluid metric (e.g., pressure level, or flow rate of the aspirated fluid) passes (e.g., exceeds) a given value (e.g., given pressure level). If fluid metric (e.g., pressure level, or flow rate of the aspirated fluid) does not pass (e.g., exceed) the given value (e.g., given pressure level or given flow rate) (branch 226), the sub-step of block 220 is repeated. If the fluid metric (e.g., pressure level, or flow rate of the aspirated fluid) passes (e.g., exceeds) the given value (e.g., given pressure level) (branch 228), the controller 74 is configured to increase (block 230) the fluid connectivity between the inlet port 66-1 and the outlet port 62-1 responsively to the fluid metric (e.g., pressure level, or flow rate of the aspirated fluid) passing (e.g., exceeding) a given value (e.g., given pressure level or given flow rate), for example, the step of block 202 is repeated.

Figure 7:
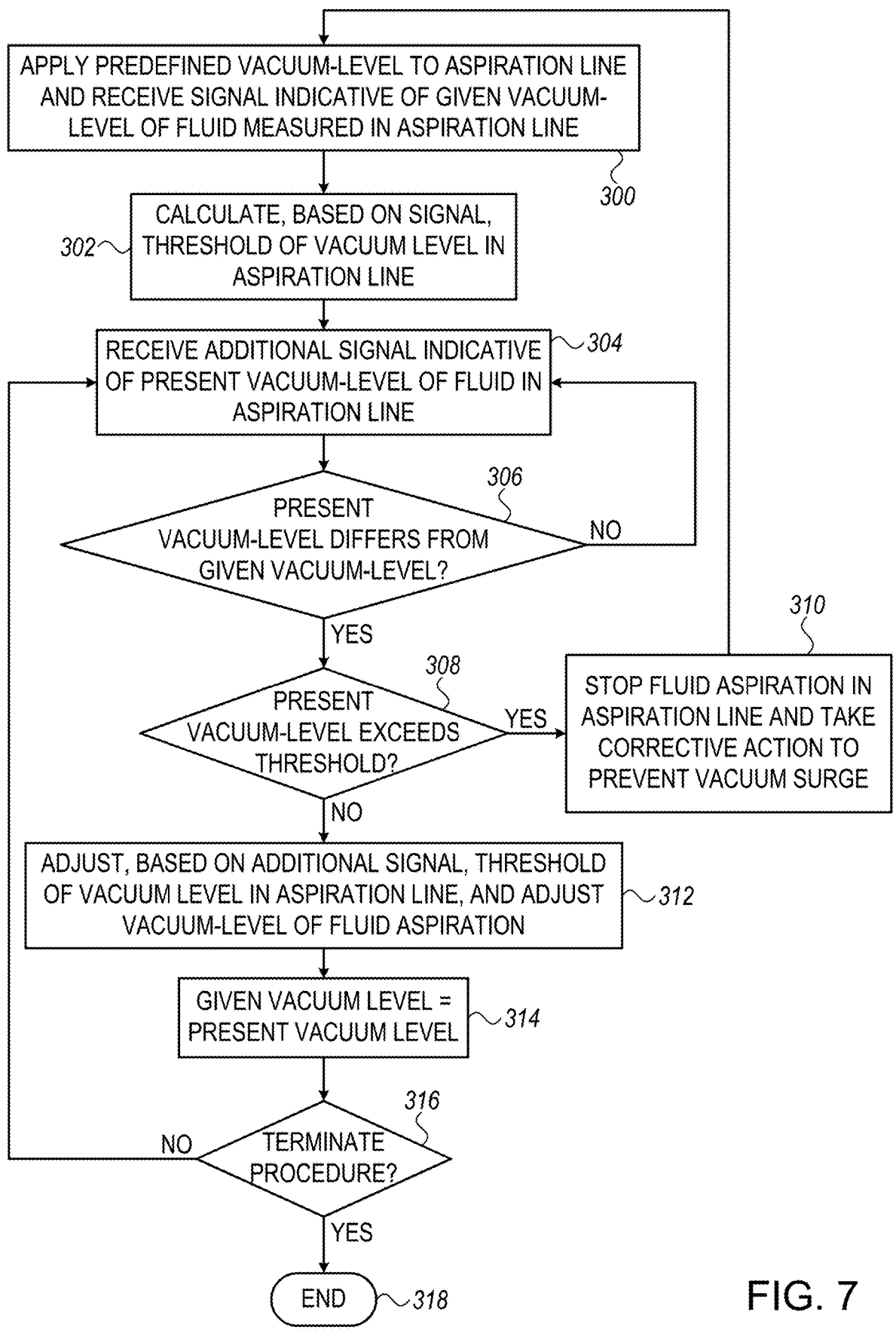
FIG. 7 is a flow chart that schematically illustrates a method for controlling intraocular pressure in patient eye during a phacoemulsification procedure, in accordance with an embodiment of the present invention.

FIG. 7 is a flow chart that schematically illustrates a method for controlling intraocular pressure (TOP) in eye 20 of patient 19 during the phacoemulsification procedure, in accordance with an embodiment of the present invention. The method begins at a fluid aspiration step 300, with physician 15 using probe 12 during the phacoemulsification procedure to apply a predefined vacuum-level to aspiration tubing line 46 and to aspiration channel 47.

The predefined vacuum-level is used for aspirating particles immersed in fluid from eye 20 through the tip of needle 16. In some embodiments, controller 74 is configured to control the operation of pumping sub-system 26 and/or the current level applied to solenoid valve 64, so as to obtain or maintain the predefined vacuum-level in aspiration tubing line 46 and aspiration channel 47.

In some embodiments, during step 300 controller 74 receives from sensor 70 a signal indicative of a given vacuum-level measured in aspiration channel 47 and in aspiration tubing line 46, as described above with reference to FIGS. 3A-3C. Controller 74 is configured to calculate one or more allowable levels of free-flow vacuum (FFV). In the context of the present disclosure, the term FFV refers to a vacuum level in which the aspirated fluid (that may contain particles) flows from eye 20 through aspiration channel 47 and aspiration tubing line 46, while retaining the desired IOP in eye 20.

At a threshold calculation step 302, controller 74 calculates, based on the signal received from sensor 70, a threshold of a vacuum level in aspiration tubing line 46 and/or aspiration channel 47. In some embodiments, the threshold may comprise a range of vacuum levels (e.g., between about 20 mmHg and 150 mmHg). Note that controller 74 calculates the vacuum-level threshold so as to enable the allowable levels of FFV described in step 300 above.

In other embodiments, the threshold of the vacuum level in aspiration tubing line 46 and/or aspiration channel 47 may be set in advance based on several parameters, such as but not limited to (i) the inner diameter of the tip of needle 16, and (ii) the required flow rate of the aspirated fluid, so as to obtain the predefined vacuum level described in step 300 above. In such embodiments, the parameters are inserted into the system and controller 74, or any other device of the system, outputs the threshold, which is inserted into controller 74. Thus, step 302 may be carried out manually before the procedure and may be eliminated from the method of FIG. 7. In alternative embodiments, the parameters may be coded into a bar-code or a quick response (QR) code associated with the cassette that could be scanned and recognized by controller 74.

At an additional signal receiving step 304, controller receives over time (i.e., while aspirating the fluid during the phacoemulsification procedure) one or more additional signal(s) indicative of the present vacuum-level of the fluid in aspiration tubing line 46 and/or aspiration channel 47. Note that during the fluid aspiration, the vacuum level may alter, for example, due to particles that may partially block aspiration channel 47 and/or aspiration tubing line 46. The altered vacuum level is the difference between the aforementioned "given" vacuum level measured in step 300 above, and the "present" vacuum level measured, at a different time interval of the phacoemulsification procedure, in step 304. In some embodiments, controller 74 is configured to store a first variable and a second variable, the first variable for storing the value of the given vacuum level, and the second variable for storing the value of the present vacuum level.

At a first comparison step 306, controller 74 compares the present vacuum level and the given vacuum level measured in aspiration tubing line 46 and/or aspiration channel 47, in steps 304 and 300, respectively. In case the present vacuum level and the given vacuum level are similar (e.g., having a difference smaller than about 3% from one another, or any other suitable difference determined by the system), the method loops back to step 304, so that the aspiration continues and controller 74 receives an additional signal from sensor 70.

In case the present vacuum level and the given vacuum level sufficiently differ from one another (e.g., the difference in vacuum level is larger than the aforementioned 3%), the method proceeds to a second comparison step 308 in which controller 74 compares between the present vacuum level, and the threshold calculated in step 302 above.

In some embodiments, in case the present vacuum-level exceeds the threshold, the method proceeds to a corrective action step 310 in which controller 74 stops the fluid aspiration in aspiration tubing line 46 and aspiration channel 47, and controls system 10 to carry out a corrective action so as to prevent the aforementioned vacuum surge. For example, controller 74 may reduce the vacuum level in aspiration tubing line 46 and in at least a portion of aspiration channel 47, by reducing the action of pumping sub-system 26, and/or by activating pumping sub-system 26 in a reversed order, also referred to herein as reflux for increasing the pressure vent in aspiration tubing line 46 and/or in aspiration channel 47, and/or by opening a vent in aspiration tubing line 46 or in aspiration channel 47, as described in FIG. 6 above. In the context of the present disclosure and in the claims, the terms "exceed" and "cross" are used interchangeably and refer to a case in which the present vacuum level surpasses the threshold.

In case the present vacuum level does not exceed the threshold, the method proceeds to an adjustment step 312 in which, based on the additional signal received from sensor 70, controller 74 is configured to dynamically learn revised allowable levels of the FFV. In some embodiments, based on the additional signal and the revised FFV level, controller 74 is configured to adjust the threshold of vacuum level in aspiration tubing line 46 and/or aspiration channel 47. In other words, the allowable FFV and the threshold are calculated based on the latest signal(s) received from sensor 70 and may be dynamically adjusted during the phacoemulsification procedure.

In some embodiments, controller 74 is further configured to adjust the vacuum-level of the fluid aspiration in aspiration tubing line 46 and/or aspiration channel 47, for example, by adjusting the current applied to solenoid valve 64.

At a variable assignment step 314, controller 74 stores the value of the present vacuum level in the variable intended for storing the value of the given vacuum level. In other words, controller 74 holds in a memory two (e.g., first and second) variables that are being updated dynamically. The value of the latest given vacuum level is stored in the first variable, and the value of the latest present vacuum level is stored in the second variable. In variable assignment step 314, controller 74 copies the value of the present vacuum level from the second variable to the first variable.

At a decision step 316, controller 74 checks whether or not at least the aspiration, and sometimes the entire phacoemulsification procedure, is concluded. In case the fluid aspiration continues, the method loops back to step 304 with sensor producing an additional signal indicative of the present vacuum level, and controller 74 stores the value of the receive signal in the variable intended for storing the value of the present vacuum level.

In case the aspiration and/or the phacoemulsification procedure are concluded, the method proceeds to a method ending step 318, which terminates the method of FIG. 7.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. An ophthalmic surgical system, comprising:
    a solenoid valve, which is positioned in the system between (i) a handle of a probe, and (ii) an aspiration line coupled with the handle for aspirating fluids from the probe, the solenoid valve comprising:
    a valve body comprising ports including an inlet port and an outlet port, a valve cavity having a direction of elongation and configured to provide fluid connectivity between respective ones of the ports;
    a solenoid coil disposed in the valve body around the valve cavity; and
    a plunger comprising a permanent magnet, and configured to move back- and-forth along the direction of elongation between a first position and a second position in the valve cavity to selectively control the fluid connectivity between respective ones of the ports;
    a sensor, which is positioned between the handle and the aspiration line and is configured to produce a signal indicative of a fluid metric in the aspiration line; and
    a controller, which is configured to identify, based on the signal, a vacuum surge in the aspiration line, and, in response to identifying the vacuum surge, to apply at least one current to the solenoid coil to selectively move the plunger between the first position and the second position, and to selectively maintain the plunger in the first position and the second position.

2. The ophthalmic surgical system according to claim 1, wherein the controller is configured to estimate a baseline value of the fluid metric based on the signal, to set a threshold depending on the baseline value of the fluid metric, and to identify the vacuum surge by detecting that the fluid metric crosses the threshold.

3. The ophthalmic surgical system according to claim 2, wherein the controller is configured to re-estimate the baseline value over time, and to adapt the threshold depending on the re-estimated baseline value.

4. The ophthalmic surgical system according to claim 2, wherein the controller is configured to set one or more additional thresholds indicative of a gradual change in the fluid metric, and to identify a change in a vacuum level in the aspiration line before the vacuum surge by detecting that the fluid metric crosses at least one of the one or more thresholds.

5. The ophthalmic surgical system according to claim 1, wherein the valve body comprises at least one shock absorber, and wherein the at least one shock absorber is configured to soften striking of the plunger against the valve body in the direction of elongation.

6. The ophthalmic surgical system according to claim 1, wherein the fluid metric comprises a pressure level of the fluid in the aspiration line, and wherein the sensor is configured to measure the pressure level.

7. The ophthalmic surgical system according to claim 1, wherein the fluid metric comprises a flow rate of the fluid aspirated in the aspiration line, and wherein the sensor is configured to measure the flow rate.

8. The ophthalmic surgical system according to claim 1, wherein, in addition to applying the at least one current to the solenoid coil, the controller is configured to apply a corrective action for reducing a vacuum level in the aspiration line.

9. The ophthalmic surgical system according to claim 8, wherein the controller is configured to reduce the vacuum level by venting the aspiration line.

10. The ophthalmic surgical system according to claim 8, wherein the controller is configured to reduce the vacuum level by controlling a pump for increasing a pressure in the aspiration line.

11. An ophthalmic surgical method, comprising:
providing an ophthalmic surgical system having a solenoid valve comprising:
- a valve body comprising ports including an inlet port and an outlet port, a valve cavity having a direction of elongation and configured to provide fluid connectivity between respective ones of the ports;
- a solenoid coil disposed in the valve body around the valve cavity; and
- a plunger comprising a permanent magnet, and configured to move back- and-forth along the direction of elongation between a first position and a second position in the valve cavity to selectively control the fluid connectivity between respective ones of the ports;

receiving a signal indicative of a fluid metric in an aspiration line coupled to a handle of a probe for aspirating fluids from the probe;

identifying, based on the signal, a vacuum surge in the aspiration line; and in response to identifying the vacuum surge, applying at least one current to the solenoid coil to selectively move the plunger between the first position and the second position, and to selectively maintain the plunger in the first position and the second position.

12. The ophthalmic surgical method according to claim 11, wherein identifying the vacuum surge comprises estimating a baseline value of the fluid metric based on the signal, setting a threshold depending on the baseline value of the fluid metric, and identifying the vacuum surge by detecting that the fluid metric crosses the threshold.

13. The ophthalmic surgical method according to claim 12, further comprising re-estimating the baseline value over time, and adapting the threshold depending on the re-estimated baseline value.

14. The ophthalmic surgical method according to claim 11, wherein the valve body comprises at least one shock absorber, and wherein the at least one shock absorber is configured to soften striking of the plunger against the valve body in the direction of elongation.

15. The ophthalmic surgical method according to claim 11, wherein the valve body comprises at least one shock absorber, and wherein the at least one shock absorber softens striking of the plunger against the valve body in the direction of elongation.

16. The ophthalmic surgical method according to claim 11, wherein the fluid metric comprises a pressure level of the fluid in the aspiration line, and wherein receiving the signal comprises measuring the pressure level.

17. The ophthalmic surgical method according to claim 11, wherein the fluid metric comprises a flow rate of the fluid aspirated in the aspiration line, and wherein receiving the signal comprises measuring the flow rate.

18. The ophthalmic surgical method according to claim 11, wherein, further comprising applying a corrective action for reducing a vacuum level in the aspiration line.

19. The ophthalmic surgical method according to claim 18, wherein applying a corrective action comprises reducing the vacuum level by venting the aspiration line.

20. The ophthalmic surgical method according to claim 18, wherein applying a corrective action comprises reducing the vacuum level by controlling a pump for increasing a pressure in the aspiration line.

* * * * *